Figure 1:
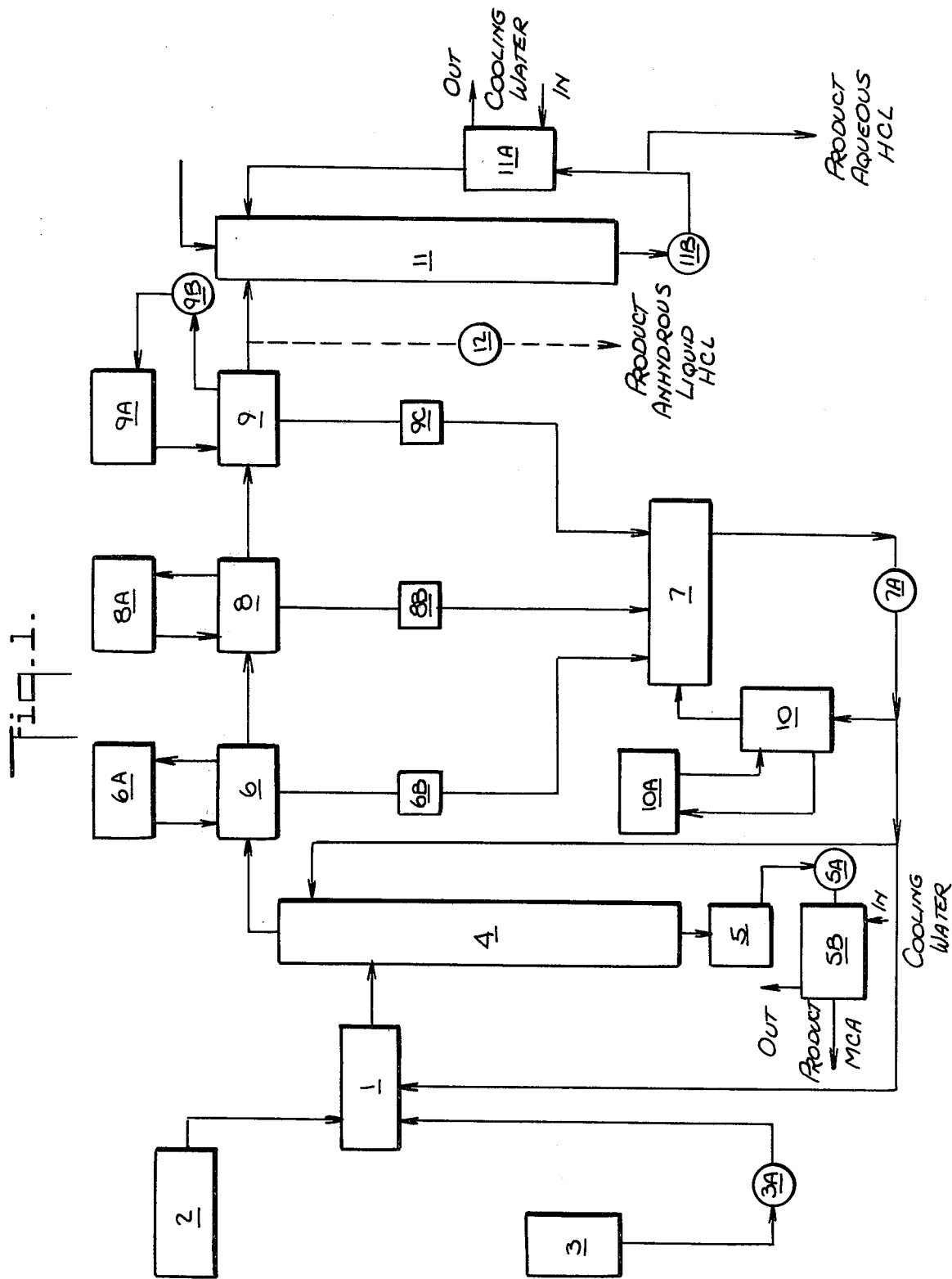

United States Patent [19]

Krieger et al.

[11] 4,439,623

[45] Mar. 27, 1984

[54] PROCESS FOR THE PREPARATION OF MONOCHLOROACETONE

[75] Inventors: Kenneth H. Krieger, Chatham; Lawrence J. Naldi, Fanwood; Carlos B. Rosas; Vijay Samant, both of Rahway, all of N.J.

[73] Assignee: Merck & Co., Inc., Rahway, N.J.

[21] Appl. No.: 308,882

[22] Filed: Oct. 5, 1981

[51] Int. Cl.$^3$ .............................................. C07C 45/62
[52] U.S. Cl. ...................................... 568/393; 203/62; 203/71
[58] Field of Search .................... 568/393; 203/71, 51, 203/62; 55/80

[56] References Cited

U.S. PATENT DOCUMENTS

| | | | |
|---|---|---|---|
| 2,116,893 | 5/1938 | Heisel | 568/393 |
| 2,234,484 | 3/1941 | Rahrs | 568/393 |
| 2,235,562 | 3/1941 | Rahrs | 568/393 |
| 2,243,484 | 5/1941 | Morey | 568/393 |
| 2,397,240 | 5/1941 | Morey | 568/393 |
| 3,397,240 | 8/1968 | Kaufman et al. | 568/393 |
| 3,761,361 | 9/1973 | Walls | 203/71 |

OTHER PUBLICATIONS

Perry, "Chem. Eng. Handbook", pp. 13–32 to 13–41, (1963).
Japan Patent 50037714 Supplied as Derwent Abstract 676251W/40.
Japan Patent 75037650 Supplied as Derwent Abstract 02840X/02.
Japan Patent 52125105 Supplied as Derwent Abstract 85528Y/48.

*Primary Examiner*—James H. Reamer
*Attorney, Agent, or Firm*—David L. Rose; Mario A. Monaco

[57] ABSTRACT

There is disclosed an improved process for the preparation of monochloroacetone by reacting acetone and chlorine in a vapor-liquid phase reactor and passing the reactor effluent through a fractionator to remove the liquid phase consisting mainly of monochloroacetone (MCA). The fractionator vapor phase effluent is consisting of acetone, hydrogen chloride, some monochloroacetone, and some reaction by-products sequentially fractionated in a series of condensers of varying temperatures such that the hydrogen chloride is isolated free of impurities and the remaining reaction materials, consisting mainly of acetone with some dissolved hydrogen chloride are available for recycling back into the reactor. The hydrogen chloride, isolated in the vapor phase, may be quenched with water to produce concentrated aqueous hydrochloric acid which may be used in other chemical procedures or it may be compressed into anhydrous hydrogen chloride. The process improvement has the advantage of eliminating all environmentally hazardous wastes such that none of the material used in the reaction is discarded as was done in the past. In addition, the improved process considerably reduces the energy requirements therefor by eliminating a costly extractive distillation step. All of the reaction products are either recycled back into the monochloroacetone reactor or are separate chemical products usable in other chemical steps.

12 Claims, 1 Drawing Figure

PROCESS FOR THE PREPARATION OF MONOCHLOROACETONE

SUMMARY OF THE INVENTION

The instant invention involves a total recycle process improvement for the manufacture of monochloroacetone. Thus, it is an object of this invention to describe said process improvement. A further object will be to describe the fractional condensers used to sequentially separate the monochloroacetone from the acetone hydrogen chloride vapor and then to separate the acetone and the hydrogen chloride in such a manner as to enable the acetone to be recycled back into the monochloroacetone reactor and to allow the production of technically pure concentrated hydrochloric acid or liquid anhydrous hydrogen chloride. A further object of this invention is to describe the condenser temperatures which have been found to optimize the fractional separation of the process effluent. A still further object is to describe a process improvement which eliminates an environmentally hazardous waste and which reduces the overall energy requirement for the process. Further objects will become apparent from a reading of the following description.

BACKGROUND OF THE INVENTION

Monochloroacetone is a chemical intermediate used in the preparation of thiabendazole. Thiabendazole is an antiparasitic agent useful for the treatment of parasitic infections in domestic animals and in humans and also an antifungal agent for use in agriculture for the prevention of fungal diseases in stored crops and grains, and also for the suppression of fungal growth in aqueous and nonaqueous systems such as paints. The chemical procedures used for the preparation of monochloroacetone are well known, see for example U.S. Pat. No. 2,116,893 to Meisel issued May 10, 1938, U.S. Pat. No. 2,235,562 to Rahrs issued Mar. 18, 1941, U.S. Pat. No. 2,234,484 to Morey issued May 27, 1941 and U.S. Pat. No. 3,397,240 to Kaufman et al. issued Aug. 13, 1968.

The current state of the art process for the preparation of monochloroacetone as described in the Kaufman et al. patent above involves the direct reaction of acetone and chlorine. The reaction is carried out in vapor phase and produces monochloroacetone in yields in excess of 90%. The reaction uses an acetone:chlorine ratio of about 10:1 thus the reaction effluent will contain monochloroacetone as well as unreacted acetone and hydrogen chloride a reaction by-product. In addition some polyhalogenated acetone may be present as well as the reaction product of hydrogen chloride and acetone-mesityl oxide. The reaction effluent is fractionated to recover the monochloroacetone in adequate purity for future use. However, fractionator effluent is quenched with water and this mixture of acetone, hydrogen chloride and water was extractively distilled yielding an acetone fraction unsuitable for recycling back into the reaction mixture and the hydrogen chloride fraction therefrom has quantities of acetone and other organic by-products to such an extent that the material was not usable for any other chemical reaction procedures. As a result, most of the reaction effluent had to be discarded owing to the presence of quantities of monochloroacetone, an extremely powerful lacrimator. The disposal of these materials presented considerable environmental problems and the extractive distillation apparatus required considerable energy input. In the instant process, all of the acetone containing small amounts of monochloroacetone and reaction by-products along with some hydrogen chloride is recycled back into the monochloroacetone reactor or into the fractionator. The hydrogen chloride which is recovered is substantially free of organic materials and may be compressed into liquid hydrogen chloride or quenched with water to form concentrated hydrocloric acid for use in other chemical procedures or for sale to those who can so use such acid.

DESCRIPTION OF THE INVENTION

This invention describes the total recycle process for the manufacture of monochloroacetone. Specifically, this process uses a unique energy efficient method with no environmentally hazardous wastes to separate the excess unreacted acetone from the by-product hydrogen chloride.

Customarily, monochloroacetone is produced by reacting chlorine with a large (approximately 10:1) stoichiometric excess of acetone. This insures the minimum formation of the polyhalogenated by-products. The reaction products, consisting mainly of monochloroacetone, unreacted acetone and by-product hydrogen chloride, are subjected to fractional distillation to separate the unreacted acetone and by-product hydrogen chloride from the monohalogenated acetone.

The essence of the total recycle process is the acetone/hydrogen chloride separation system which consists of a triple partial condenser system operating on a descending temperature order. Such a multipartial condenser system effects the separation of acetone from hydrogen chloride by condensing all the acetone. The condensed acetone, containing some dissolved hydrogen chloride, is suitable for recycling back to the monochloroacetone reactor and the fractionator. The purpose of the multipartial condenser system is to produce hydrogen chloride free of organic impurities and to shift the maximum energy load to the primary condenser, where the greatest condensate load is found, and to shift the energy load away from the low temperature condenser where the operational cost per unit of material passing through the condenser is highest. In addition the amount of hydrogen chloride being returned to the reactor is reduced thus minimizing the formation of by-products.

Referring now to the drawing FIG. I, 1 is the vapor-liquid phase reactor for the preparation of monochloroacetone. The reactor 1 is supplied with chlorine from 2, acetone from 3 and recycled acetone from reflux drum 7. After the reaction and the preparation of monochloroacetone, all of the product, by-products and excess reactants are sent to the fractionator 4. The monochloroacetone is fractionated and enters the reboiler 5 where it is removed by pump 5a and cooled in the cooling unit 5b. The monochloroacetone is continuously removed from the reboiler at a purity of from 90–92%. The effluent from the fractionator 4, distilled in the vapor phase, enters the first condenser 6 where acetone, containing some hydrogen chloride and other reaction by-products, is condensed and enters reflux drum 7. The temperature of condenser 6 is maintained by the temperature control bath 6a. The vapor phase effluent from condenser 6 enters condenser 8 controlled by temperature control bath 8a. The liquid condensate from condenser 8, consisting of acetone containing some hydrogen chloride, also enters reflux drum 7. The vapor phase effluent from condenser 8 enters condenser 9 whose temperature is maintained by a temperature control bath 9a and pump 9b. The liquid condensate from condenser 9 also enters reflux drum 7. Reflux drum 7, containing acetone, hydrogen chloride and a minor amount of reaction by-products, is cooled with heat exchanger 10 preferably a freon cooled heat exchanger and maintained by temperature controller 10A. The temperature of reflux drum 7 is maintained at from 0° to −30° C., preferably at from 0° to −5° C., to reduce the reaction rate between acetone and hydrogen chloride in the formation of mesityl oxide. The material is recycled into the monochloroacetone reactor 1 or into both the reactor and the fractionator 4. If desired 100% of the outflow from the reflux drum 7 may be recycled into the reactor 1. However, if desired, to improve the operational characteristics of the fractionator 4, up to 35% of the reflux drum 7 outflow may be sent to the fractionator 4. The vapor phase effluent from condenser 9, consisting of only hydrogen chloride with less than 1,000 parts per million of organic matter, may be quenched in water in absorber 11 using the heat exchanger 11a to remove the exothermic heat of solution. The aqueous acid produced thereby is usable as a source of concentrated hydrochloric acid. Optionally, the vapor phase effluent from condenser 9 may be compressed in compressor 12 into liquid aqueous hydrogen chloride and used in that form if desired.

The condensate from condensers 6, 8 and 9 is generally preferred to pass through liquid seals 6B, 8B and 9C prior to entering the reflux drum 7. This insures that vapor from the condenser is not allowed to enter the reflux drum or to contaminate the other condensers.

In carrying out the foregoing process improvements, it has been discovered that not only as the environmental problem of disposing of hazardous acidic wastes been avoided but that the total energy usage of the condenser system of the improved process is significantly lower than the energy usage of the prior process. The improved process uses ⅓ the energy of the previous process. Thus, the recovery of usable by-products, the recycling of reaction product, the avoidance of environmentally hazardous wastes and the reduction in energy consumption discovered by the use of the instant process is a significant improvement, especially in view of the current concerns towards energy wastes and environmental purity.

The 3-stage condensation of the vapor phase effluent from the fractionater is carried out such that the condenser 6 is maintained at a temperature of from 40°-55°. Preferably the condenser is maintained at from 50° to 55° C. Optimally, the condenser is maintained at about 52° C. The first condenser is generally maintained at these temperatures with a water-cooled bath. The second stage of condensation carried out in condenser 8 is done at a temperature of from 10°-35° C., preferably at from 25° to 30° C. Optimally, the temperature is maintained at about 28° C. The second condenser is generally maintained at these temperatures with a brine or ethylene glycol cooled bath. The third stage condenser is maintained at a temperature which will remove substantially all of the acetone remaining in the acetone/hydrogen chloride vapor mixture. Temperatures of −20° C. or less are utilized. The minimum temperature is determined on the basis of the cost required to maintain temperature controlled bath 9a at the lowest temperature feasible. Generally, temperatures from −20° to −40° C. are economically preferable. It is more preferred to maintain the condenser at about −25° to −35° C. Optimally, the condenser 9 is maintained at −30° C. The third condenser is generally maintained at this temperature with a dry-ice/acetone bath or freon cooling unit.

In using the instant multipartial condenser system, it has been found that the energy input distribution among the three condensers is about 80% to the first condenser, 19% to the second condenser and 1% to the third condenser. Thus the energy load is shifted away from the condenser bearing the highest energy usage rate and the smallest product load, towards the condenser with the lowest energy usage rate and highest product load. In this manner the energy efficiency of the system is optimized and the total energy usage for the system minimized.

The following example is provided in order that the instant process and the improvement thereof may be more fully understood. The example is not to be considered as restrictive of the instant invention.

EXAMPLE

60 Grams/hr of dry chlorine gas was continuously reacted co-currently with 490 gms/hr of liquid acetone in a tubular reactor of 2 mm internal diameter and 25 mm length. The acetone entering the reactor consisted of a mixture of 441 gms/hr of recycled acetone at 0° C. containing 32.2 mole% dissolved hydrogen chloride (HCl) and 49 gms/hr of fresh acetone at 25° C. containing 0.4 wt.% water. The acetone to chlorine mole ratio in the reactor was 10:1. The vapor-liquid mixture from the reactor consisting mainly of monochloroacetone (MCA), unreacted acetone and HCl was fed continuously to the 10th plate of a 15 plate, 28 mm ID vaccum jacketed, oldershaw fractionator column. The MCA formed in the reactor having a high boiling point (bp 118° C.) was continuously collected in the reboiler at the bottom of the column, which was maintained at 110° C. The overhead vapors of the fractionator column consisting of unreacted acetone and HCl were totally condensed in a series of three condensers. The first condenser called the primary condenser was a downflow water cooled, double pass unit operating at a temperature of 45° C. and condensed ca. 353 g/hr of acetone with a dissolved HCl content of 29.9 mole%. The secondary condenser was an ethylene glycol cooled, double pass, downflow condenser operating at a temperature of 13° C. and condensed ca. 85 gms/hr of acetone with a dissolved HCl content of 46.5 mole%. The tertiary condenser was a single pass, upflow, 'dry ice-acetone' cooled condenser operating at a temperature of −25° C. and condensed 3 gms/hr of acetone with a dissolved HCl content of 64 mole%. The condensates from each of the condensers flowed into a 200 ml jacketed reflux drum and the contents of the drum were maintained at 0° C. by recirculating through an external freon cooled, single pass condenser. The reflux drum was maintained at a constant level of 50 ml and the condensed acetone/HCl mixture was returned 65% to the reactor as recycle, and 35% to the fractionator column as reflux. The reflux was returned to the top of the column for a reflux ratio of 0.8 and the recycle was returned back to the MCA reactor. The HCl gas leaving the tertiary condenser at −25° C. was absorbed co-currently in a 30 mm ID vigreaux column to produce 20° Braume hydrochloric acid (concentrated hydrochloric acid). The monochloroacetone product was withdrawn continuously as liquid from the reboiler at 90.5% purity.

What is claimed is:

1. In a process for the continuous vapor-liquid phase production of monochloroacetone from chlorine and acetone in a reactor and removing the monochloroacetone from the reaction stream in a fractionator, the improvement comprises passing the vapor phase effluent from the fractionator sequentially through a series of 3 temperature controlled condensers with decreasing temperature ranges wherein:

A. the first condenser in maintained at a temperature of from 40° to 55° C. and the condensate therefrom enters a common reflux drum and the vapor phase effluent enters the second condenser;
   B. the second condenser in maintained at a temperature of from 10° to 35° C. and the condensate therefrom enters the same common reflux drum as the condensate from the first condenser, and the vapor phase effluent therefrom enters the third condenser;
   C. the third condenser is maintained at a temperature of from −20° to −40° C. and the condensate therefrom enters the same common reflux drum as the condensate from the first and second condensers and the vapor phase effluent therefrom consisting entirely of hydrogen chloride is isolated; and
   D. the contents of the common reflux drum are fed continuously back into the reactor or to both the reactor and the fractionator for the production of monochloroacetone.

2. The improved process of claim 1 wherein the first condenser is maintained at from 50° to 55° C.

3. The improved process of claim 2 wherein the first condenser is maintained at about 52° C.

4. The improved process of claim 1 wherein the second condenser is maintained at from 25° to 30° C.

5. The improved process of claim 4 wherein the second condenser is maintained at about 28° C.

6. The improved process of claim 1 wherein the third condenser is maintained at from −25° to −35° C.

7. The improved process of claim 1 wherein the third condenser is maintained at about −30° C.

8. The improved process of claim 1 wherein the material contained in the common reflux drum is maintained at from 0° to 30° C.

9. The improved process of claim 8 wherein the material contained in the common reflux drum is maintained at from 0° to −5° C.

10. The improved process of claim 1 wherein the condensate from each of the 3 condensers passes through a liquid seal prior to entering the common reflux drum.

11. The improved process of claim 1 wherein the outflow from the common reflux drum is entirely recycled back into the monochloroacetone reactor.

12. The improved process of claim 1 wherein the outflow from the common reflux drum is divided such that up to 35% thereof enters the fractionator as reflux and the remainder enters the monochloroacetone reactor as recycle.

* * * * *